| United States Patent [19] | [11] Patent Number: 4,578,468 |
| Carter et al. | [45] Date of Patent: Mar. 25, 1986 |

[54] ANTIBIOTIC LL-D42067β

[75] Inventors: Guy T. Carter; Donald B. Borders, both of Suffern; Joseph J. Goodman, Spring Valley, all of N.Y.; David P. Labeda, Peoria, Ill.

[73] Assignee: American Cyanamid Company, Stamford, Conn.

[21] Appl. No.: 593,159

[22] Filed: Mar. 26, 1984

[51] Int. Cl.$^4$ .......................................... C07D 498/12
[52] U.S. Cl. ................................... 546/35; 514/279; 435/118; 546/34
[58] Field of Search ................................... 546/35, 34

[56] References Cited

U.S. PATENT DOCUMENTS 4,551,533  11/1985  Lee et al. .................. 546/35

OTHER PUBLICATIONS

Merck Index, 9th edition, 200, p. 29.

Primary Examiner—Donald G. Daus
Assistant Examiner—Cecilia Shen
Attorney, Agent, or Firm—Anne M. Rosenblum; Susan H. Rauch

[57] ABSTRACT

Antibiotic LL-D42067β derived by aerobic fermentation of the microorganism *Actinomadura madurae* subspecies *simaoensis* NRRL 15734, useful as an antibacterial and antiparasitic agent.

1 Claim, 4 Drawing Figures

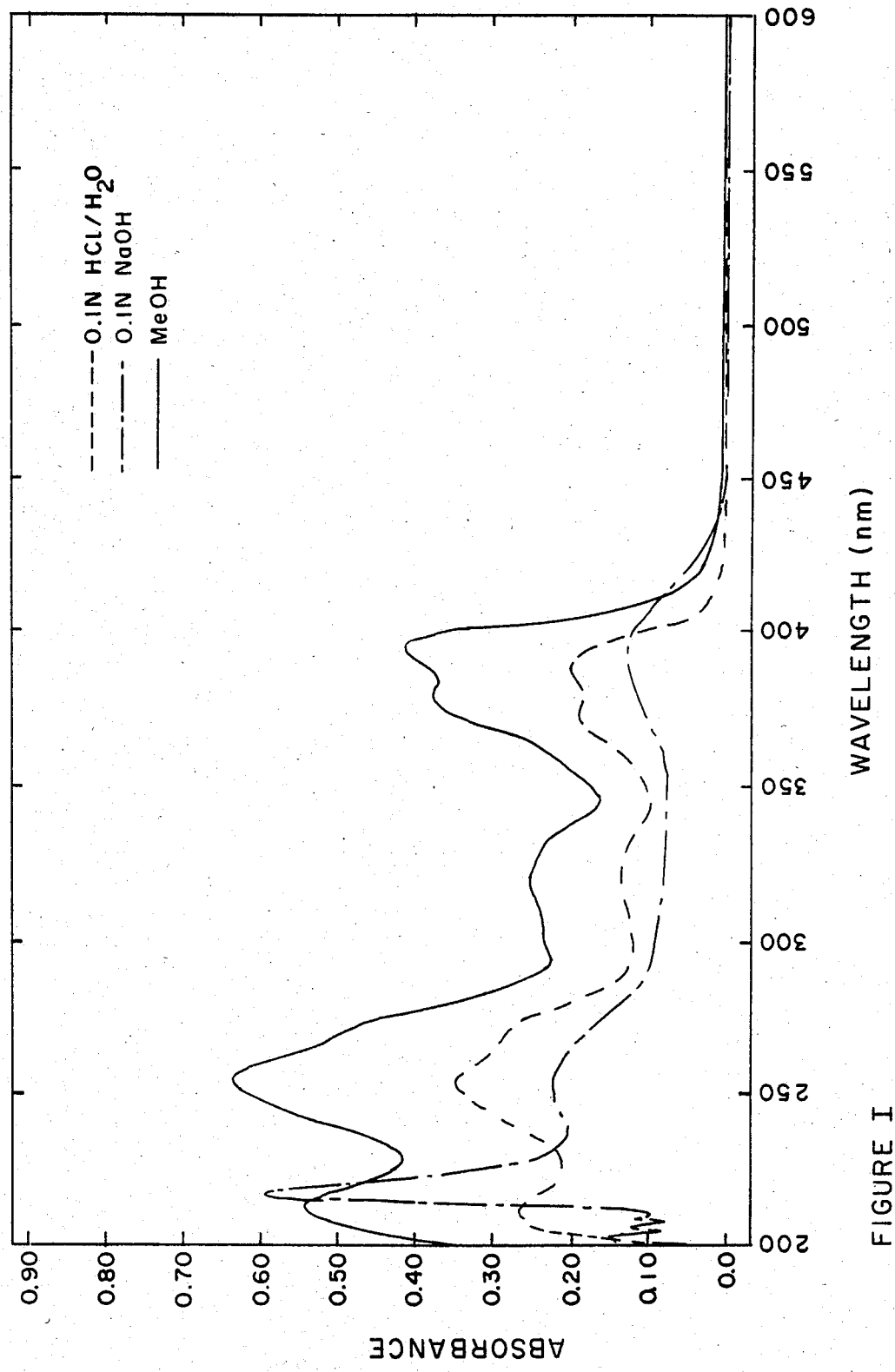
FIGURE I

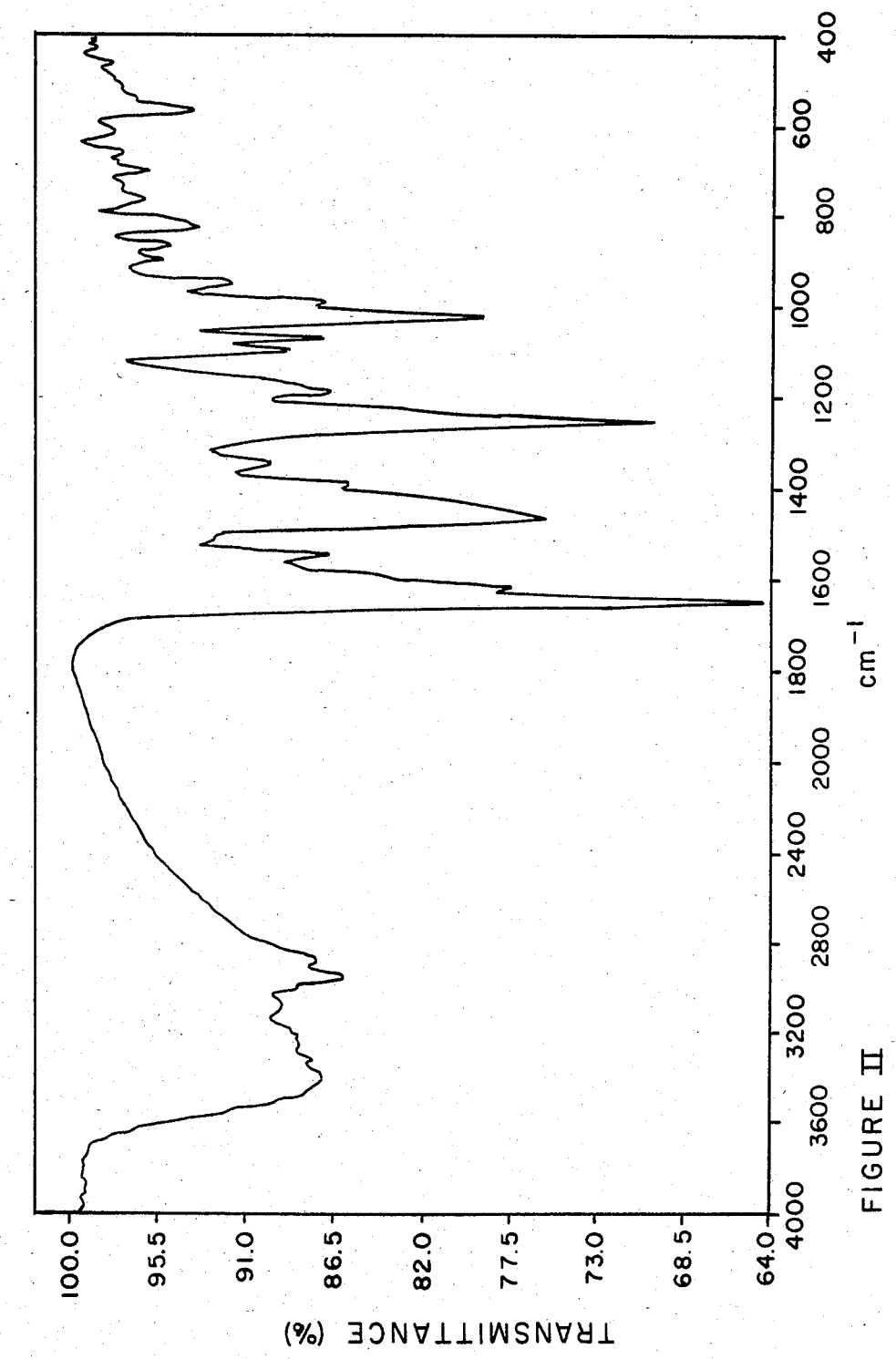

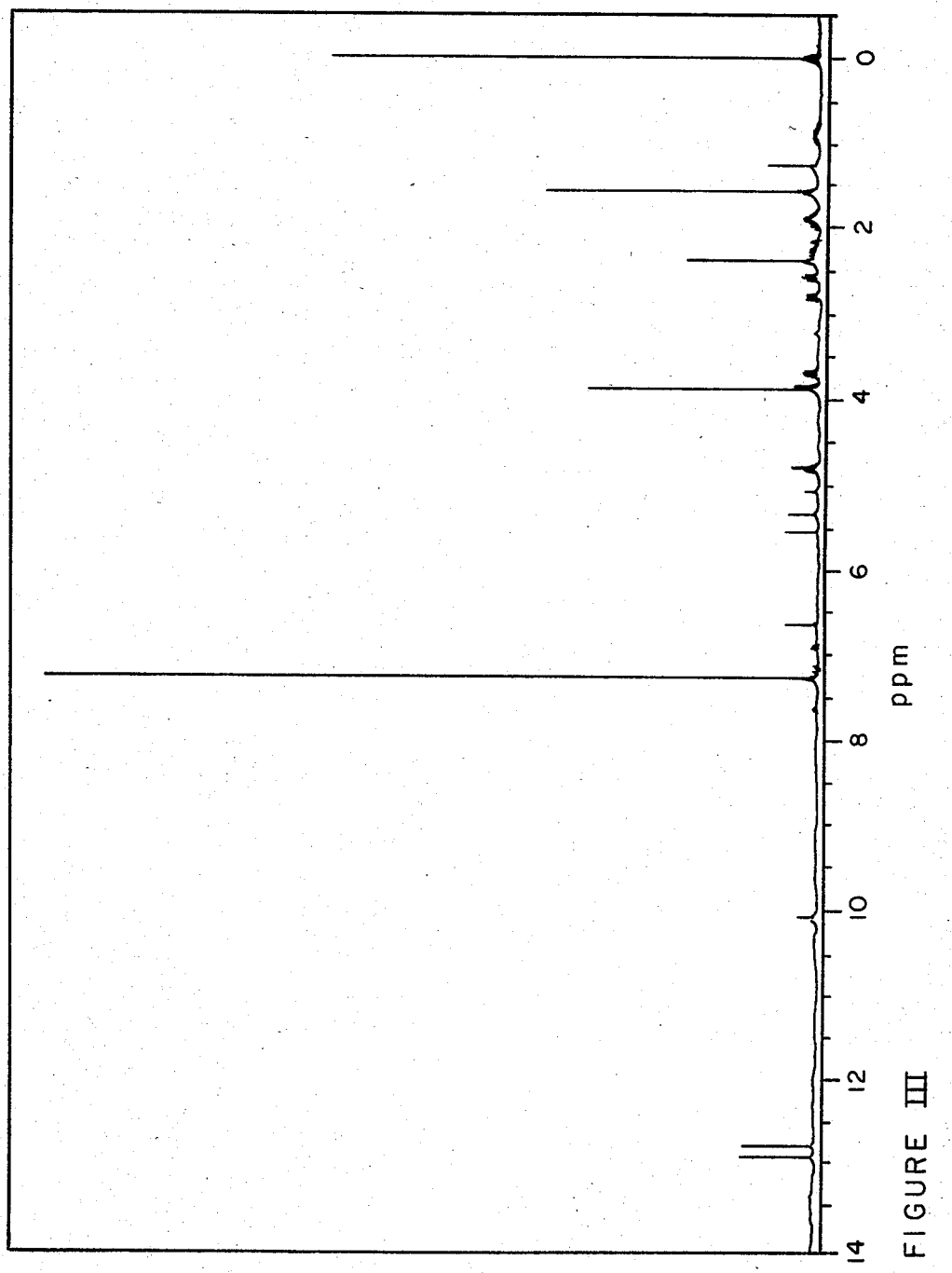
FIGURE III

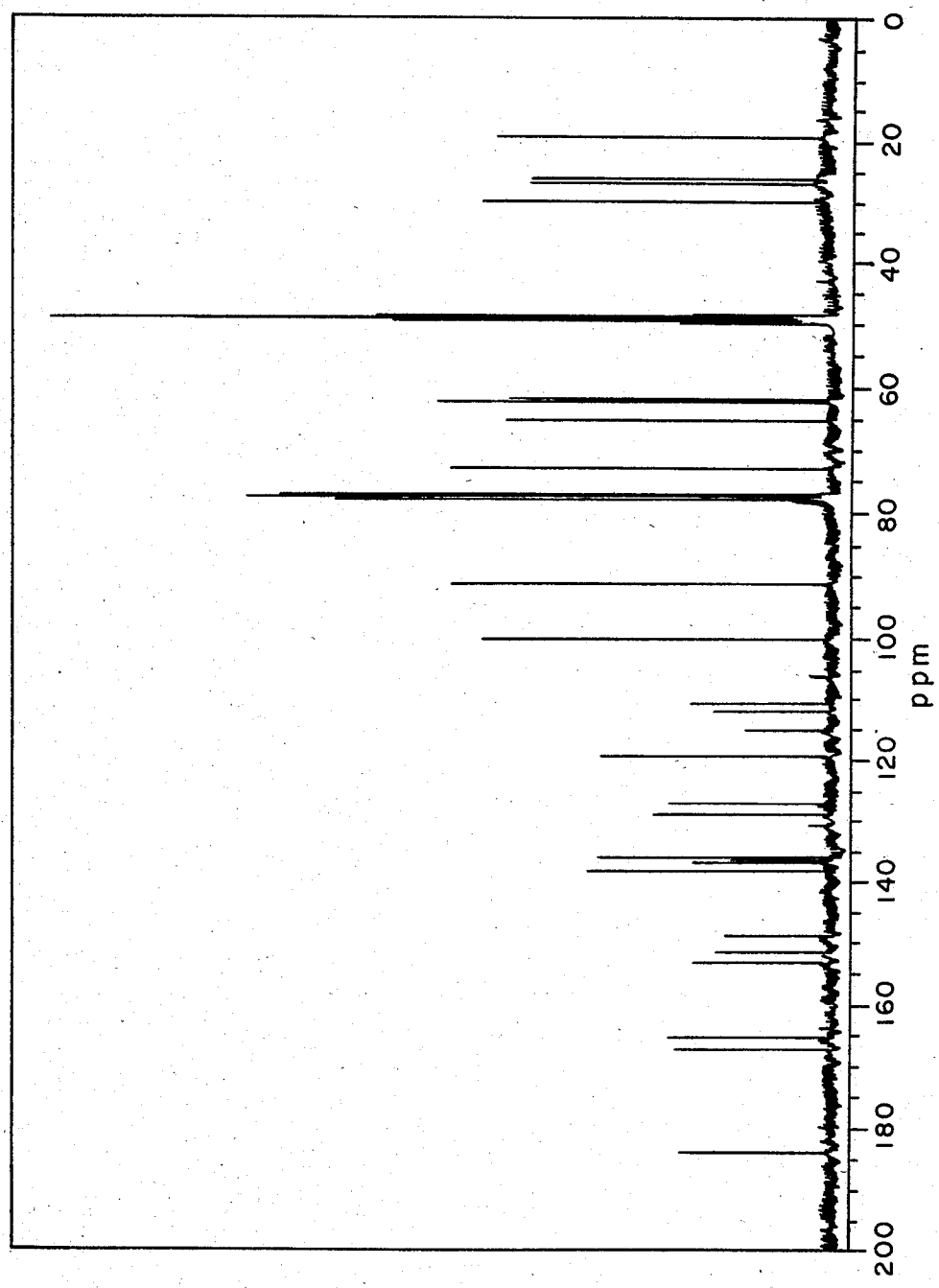

ANTIBIOTIC LL-D42067β

SUMMARY OF THE INVENTION

This invention relates to a new antibacterial and antiparasitic agent designated LL-D42067β, to its production by fermentation, to methods for its recovery and concentration from crude solutions and to processes for its purification. The present invention includes within its scope the biologically pure culture which produces the antibiotic.

The structure and relative stereochemistry of LL-D42067β have been elucidated and is shown below.

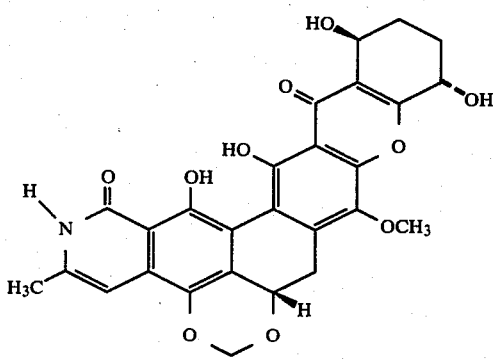

The physico-chemical characteristics of LL-D42067β are described below:

(1) Molecular weight: 521 (FAB-MS)

(2) Molecular formula: $C_{27}H_{23}NO_{10}$ (3) Specific optical rotation: $[\alpha]_D^{26} = +770\pm°$ (C 0.165, DMF);

(4) Ultraviolet absorption spectra: as shown in FIG. I
$UV_{MAX}^{CH3OH} = 212$ nm ($\epsilon$ 28,200), 253 nm ($\epsilon$ 33,200), 318 nm ($\epsilon$ 13,200), 378 nm ($\epsilon$ 19,700), 393 nm ($\epsilon$ 21,700).
$UV_{MAX}^{0.1N\ HCl} = 211$ nm ($\epsilon$ 13,900), 253 nm ($\epsilon$ 18,200), 318 nm ($\epsilon$ 7,140), 372 nm ($\epsilon$ 9,950), 388 nm ($\epsilon$ 10,500).
$UV_{MAX}^{0.1N\ NaOH} = 216$ nm ($\epsilon$ 31,200), 251 nm ($\epsilon$ 11,700).

(5) Infrared absorption spectrum: as shown in FIG. II (KBr disc): 3400, 1646, 1620, 1545, 1463, 1252, 1195, 1020 cm$^{-1}$;

(6) Proton nuclear magnetic resonance spectrum (CDCl$_3$): as shown in FIG. III, and described in Table I;

(7) Carbon-13 nuclear magnetic resonance spectrum (CD$_3$OD/CDCl$_3$): as shown in FIG. IV and described in Table II.

TABLE I

| | Proton NMR Data for LL-D42067β | | |
|---|---|---|---|
| δ* | No. of Hydrogen | Multiplicity** | J (H) |
| 1.88 | 2 | m | |
| 2.30 | 2 | m | |
| 2.38 | 3 | s | |
| 2.57 | 2 | m | |
| 3.69 | 1 | d,d | 4.5, 14.3 |
| 3.87 | 3 | s | |
| 4.79 | 1 | m | |
| 4.81 | 1 | d,d | 4.5, 12.7 |
| 5.06 | 1 | m | |
| 5.32 | 1 | d | 5.8 |
| 5.53 | 1 | d | 5.8 |
| 6.54 | 1 | s | |
| 10.1 | 1 | s | |
| 12.8 | 1 | s | |
| 12.9 | 1 | s | |

*CDCl$_3$, ppm downfield from TMS.
**s = singlet; d = doublet; m = multiplet.

TABLE II

| Carbon-13 NMR Data for LL-D42067β | |
|---|---|
| Carbon | Chemical Shift (ppm)* |
| 1 | 19.1 |
| 2 | 25.9 |
| 3 | 26.9 |
| 4 | 29.7 |
| 5 | 62.0 |
| 6 | 62.2 |
| 7 | 65.0 |
| 8 | 72.8 |
| 9 | 91.1 |
| 10 | 100.1 |
| 11 | 110.5 |
| 12 | 110.6 |
| 13 | 111.7 |
| 14 | 114.7 |
| 15 | 119.2 |
| 16 | 127.2 |
| 17 | 128.8 |
| 18 | 136.1 |
| 19 | 136.3 |
| 20 | 137.0 |
| 21 | 138.1 |
| 22 | 148.9 |
| 23 | 151.9 |
| 24 | 153.0 |
| 25 | 165.3 |
| 26 | 167.2 |
| 27 | 183.6 |

*CD$_3$OD/CDCl$_3$, ppm downfield from TMS.

DETAILED DESCRIPTION OF THE INVENTION

The new antibacterial agent designated LL-D42067β is formed during the cultivation under controlled conditions of a new strain of a new subspecies of *Actinomadura madurae*. This new strain is maintained in the culture collection of the Medical Research Division, American Cyanamid Company, Pearl River, N.Y. as culture number LL-D42067. A viable culture of this new microorganism has been deposited with the Patent Culture Collection Laboratory, Northern Regional Research Center, U.S. Department of Agriculture, Peoria, Ill. 61604, and has been added to its permanent collection. It is freely available to the public in this depository under its accession number NRRL 15734.

Culture LL-D42067 was isolated from a soil sample from San Simao, Brazil. The culture was taxonomically characterized and was identified as a new subspecies of *Actinomadura madurae*, designated *Actinomadura madurae* subspecies *simaoensis*.

Observations were made of the cultural, physiological and morphological features of the culture in accordance with the methods detailed by Shirling and Gottlieb [Intern. J. System, Bacteriol., 16:313-340 (1966)] and Gordon, et al. [Intern. J. System. Bacteriol., 24:54-63 (1974)]. The chemical composition of the cell walls of the culture was determined using the method of Lechevalier, et al. [Adv. Appl. Microbiol., 14:47-72 (1971)]. Details are recorded in Tables III-V, and a general description of the culture is given below. Underscored descriptive colors are taken from Kelly and Judd [Nat. Bur. Stand., Spec. Publ., 440 (1976)] and the accompanying Intersociety Color Council, National Bureau of Standards Centroid Color Charts. *Growth Characteristics*

Table III describes the cultural characteristics of culture LL-D42067 on various agar media which were selected from those recommended by the International Streptomyces Project Committee (hereinafter referred to as "ISP").

Micromorphology

Microscopic examination of the strain showed it to form short chains of conidia on aerial hyphae which were slightly hooked to short-spirals (up to three turns). The spore surfaces were smooth when observed by electron microscopy, distinguishing this isolate from *A. verrucosopora*.

Cell Wall Composition

Whole cell analyses showed the strain to contain meso diaminopimelic acid (DAP) and the sugar 3-O-methyl-D-galactose (madurose); thus it falls into whole cell pattern type B. The cell wall composition was of the type III (meso DAP, glutamic acid, alanine, muramic acid and glucosamine) and the phospholipid pattern of type PIV (phosphatidyl ethanolamine and/or methylethanolamine plus unknown glucosamine-containing phospholipids). These data support the assignment of the strain to the genus Actinomadura. The PIV phospholipid type is not typical for *A. madurae*, which is usually PI.

Physiological Reactions

The physiological reactions of strain LL-D42067 were examined using both the ISP system, Shirling and Gottlieb [Intern. J. Syst. Bacteriol., 16:313–340 (1966)] and the Gordon tests, Gordon, et al. [Intern. J. Syst. Bacteriol., 24:54–63 (1974)]. The utilization pattern of the strain on ISP carbohydrate media is given in Table IV, along with those of other members of the genus reacting similarly. Culture LL-D42067 resembles the *Actinomadura madurae* and *Actinomadura verrucosopora* groups. As indicated above, however, it differs from *Actinomadura verrucosopora* in having smooth spore walls. A comparison of reactions in the Gordon test series of *Actinomadura madurae* (Gordon's data; see reference above) and LL-D42067, summarized in Table V, revealed differences only in amylase production and acid from glycerol and raffinose. Since amylase production and raffinose utilization have been found to be variable in *Actinomadura madurae* [Goodfellow, N., et al., J. Gen. Microbiol., 112:95–111 (1979)], the glycerol reaction remains the only physiological difference of LL-D42067 from this taxon.

Since strain LL-D42067 is the same as *Actinomadura madurae* in all properties evaluated except for its glycerol reaction and its PIV phospholipid pattern, it has been assigned to the taxon *Actinomadura madurae* as a subspecies designated *Actinomadura madurae* subspecies *simaoensis*.

TABLE III

Cultural Characteristics of LL-D42067 *Actinomadura madurae* subspecies *simaoensis* on ISP Morphological Media

| Agar Medium | Aerial Mycelium | Vegetative Mycelium | Soluble Pigment |
|---|---|---|---|
| Yeast extract, Malt extract (ISP 2) | White, sparse | Medium orange-brown-I53* | None |
| Inorganic Salts Starch (ISP 4) | Colorless | Colorless | None |
| Glucose Asparagine (ISP 5) | Colorless | Colorless | None |
| Oatmeal (ISP 3) | Sparse pinkish-white | Light Orange-brown-I52* | None |

*I = ISCC Color charts

TABLE IV

Comparison of Carbohydrate Utilization Reactions of LL-D42067 With Related Actinomadura spp.

| Carbohydrate | LL-D42067 | *A. madurae* (a) | *A. verrucosopora* (a) (b) |
|---|---|---|---|
| L-arabinose | + | + | + |
| D-fructose | + | + | + |
| I-inositol | − | variable | variable |
| D-mannitol | + | + | + |
| raffinose | − | − | − |
| rhamnose | + | + | + |
| sucrose | + | + | + |
| D-xylose | + | + | + |

(a) Goodfellow, M., et al., J. Gen. Microbiol., 112:95–111 (1979).
(b) Nonomura, H. and O'Hara, Y., J. Ferm. Technol., 49:904–912 (1971).

TABLE V

Gordon Test Reactions of LL-D42067

| | LL-D42067 | *A. madurae* (Gordon Data*) |
|---|---|---|
| Degradation/Transformation of | | |
| Casein | + | +(98) |
| Xanthine | − | − |
| Hypoxanthine | + | +(98) |
| Tyrosine | + | +(91) |
| Adenine | − | − |
| Production of | | |
| Amylase | − | + |
| Gelatinase | + | + |
| Phosphatase | − | ND |
| Nitrate Reductase | + | +(98) |
| Urease | − | − |
| Esculinase | + | +(98) |
| Growth on/in | | |
| 5% Sodium Chloride | − | ND |
| Salicylate | − | ND |
| Lysozyme Broth | − | −(91) |
| Utilization | | |
| Acetate | + | + |
| Benzoate | − | −(94) |
| Citrate | − | +(83) |
| Lactate | + | ND |
| Malate | + | +(84) |
| Mucate | − | − |
| Oxalate | − | ND |
| Propionate | − | ND |
| Pyruvate | + | ND |
| Succinate | + | +(83) |
| Tartrate | − | − |
| Growth at | | |
| 10° C. | − | − |
| 45° C. | + | −(66) |
| 53° C. | − | − |
| Acid from | | |
| Adonitol | + | +(91) |
| Arabinose | + | + |
| Cellobiose | + | + |
| Dextrin | + | ND |
| Dulcitol | − | − |
| Erythritol | − | − |
| Fructose | + | ND |
| Galactose | + | +(84) |
| Glucose | + | + |

TABLE V-continued
Gordon Test Reactions of LL-D42067

|  | LL-D42067 | A. madurae (Gordon Data*) |
|---|---|---|
| Glycerol | − | + |
| Inositol | − | +(60) |
| Lactose | − | +(55) |
| Maltose | − | +(53) |
| Mannitol | + | + |
| Mannose | + | +(94) |
| Melibiose | − | − |
| α-Methyl-D-glucoside | − | − |
| Raffinose | variable | − |
| Rhamnose | + | + |
| Salicin | + | ND |
| Sorbitol | − | − |
| Sucrose | + | ND |
| Trehalose | + | +(96) |
| Xylose | + | + |
| β-Methyl-D-xyloside | + | ND |

*Percentages of cultures showing reaction given in parentheses if not 100%.
ND = Not determined.

For the production of this new antibacterial and antiparasitic agent the present invention is not limited to this particular organism or to organisms fully answering the above growth and microscopic characteristics, which are given for illustrative purposes only. In fact, it is desired and intended to include the use of naturally-occurring mutants of this organism as well as induced mutants produced from this organism by various mutagenic means known to those skilled in the art such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techniques known to those skilled in the art such as, for example, a conjugation, transduction and genetic engineering techniques.

The in vitro antimicrobial spectrum of LL-D42067β was determined by the agar plate dilution method with Mueller-Hinton agar and an inoculum of each test organism of approximately $10^4$ colony forming units delivered by the Steers replicating device. The minimal inhibitory concentration (MIC) in mcg/ml was defined as the lowest concentration of LL-D42067β that inhibited visible growth after 18 hours incubation at 35° C.

The results, summarized in Table VI, show that LL-D42067β was active versus gram-positive bacteria and moderately active against yeasts.

TABLE VI
Antimicrobial Spectrum of LL-D42067β

| Test Organism |  | MIC(mcg/ml) |
|---|---|---|
| Candida albicans | CA 300 | 512 |
| Saccharomyces cerevisiae | Y 15 | 512 |
| Mycobacterium smegmatis | ATCC 607 | 512 |
| Bacillus subtilis | ATCC 6633 | 4 |
| Bacillus cereus | LL No. 4 | ≦0.06 |
| Enterococcus | OSU 75-1 | 1 |
| Enterococcus | SM 77-15 | 2 |
| Streptococcus faecalis | ATCC 29212 | 1 |
| Streptococcus mutans | ATCC 27352-1 | 0.25 |
| Streptococcus mutans | BHI (b) | 0.25 |
| Streptococcus sanguis | G9B (a) | 0.5 |
| Staphylococcus epidermidis | CMC 83-56 | 0.5 |
| Staphylococcus epidermidis | ATCC 12228 | 0.25 |
| Staphylococcus aureus | Smith | 0.5 |
| Staphylococcus aureus | LL No. 14 | 0.5 |
| Staphylococcus aureus | LL No. 27 | ≦0.06 |
| Staphylococcus aureus | LL No. 45 | 0.12 |
| Staphylococcus aureus | ATCC 25923 | 0.25 |
| Micrococcus luteus | PC 1001 | ≦0.06 |
| Escherichia coli | No. 311 | 512 |
| Escherichia coli | ATCC 25922 | 512 |
| Acinetobacter calcoaceticus | STFD 79-17 | 512 |

The antibiotic LL-D42067β derives utility from its antibacterial and antiparasitic activities. For example, the antibiotic may be used in the suppression of intestinal bacterial flora, as a topical antibacterial agent or antiseptic against gram-positive bacteria and as a general disinfectant for surfaces such as instruments. It may also be useful as an antiprotozoal agent in the treatment of malaria. In addition to its antimicrobial and antiparasitic activity LL-D42067β is effective as an anticoccidial agent in poultry. This utility is the subject of a copending application for United States Letters Patent.

In therapeutic use, the compound of this invention may be administered in the form of conventional pharmaceutical compositions appropriate for the intended use. Such compositions may be formulated so as to be suitable for oral or topical administration. The active ingredient may be combined in admixture with a non-toxic pharmaceutically acceptable carrier, which carrier may take a wide variety of forms depending on the form of preparation desired for administration, i.e., oral or topical.

General Fermentation Conditions

Cultivation of *Actinomadura madurae* subspecies *simaoensis* NRRL 15734 may be carried out in a wide variety of liquid culture media. Media which are useful for the production of this novel antibiotic LL-D42067β include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

General Procedure for the Isolation of LL-D42067β

Antibiotic LL-D42067β is recovered from the whole harvest mash by filtration through a medium such as diatomaceous earth, extraction into a solvent such as ethyl acetate, concentration to a syrup, partitioning between heptane and methanol and concentration of the methanol phase to a residue. This residue is triturated with hexane, then concentrated to a residue which is dissolved in a mixture of equal parts acetonitrile and water and then evaporated giving a precipitate. This precipitate is purified by preparative reverse phase high performance liquid chromatography (HPLC) using the system acetonitrile:water:acetic acid (3000:6000:5). The active fractions are combined, evaporated to an aqueous suspension and extracted with ethyl acetate which is evaporated to obtain the pure LL-D42067β.

EXAMPLE 1

Inoculum Preparation

A typical medium used to grow the various stages of inoculum was prepared according to the following formula:

| Dextrose | 1.0% |
|---|---|
| Dextrin | 2.0% |
| Yeast extract | 0.5% |
| NZ Amine A ®[1] | 0.5% |
| Calcium carbonate | 0.1% |
| Water qs | 100% |

[1] A pancreatic digest of casein, registered trademark of Sheffield Chemical, Norwich, New York]

This medium was sterilized. A 100 ml portion of this sterile medium, in a flask, was inoculated with mycelial scrapings from an agar slant of *Actinomadura madurae* subspecies *simaoensis* NRRL 15734. The medium was then agitated vigorously on a rotary shaker for 48–72 hours at 28° C. providing primary inoculum. This primary inoculum was then used to inoculate 10 liters of the above sterile medium, which was then grown at 28° C. for 48 hours, providing secondary inoculum. This secondary inoculum was then used to inoculate 20 liters of the above sterile medium, in a tank, which was grown for 48 hours at 28° C. with a flow of sterile air of 200 liters per minute, providing tertiary inoculum.

EXAMPLE 2

Fermentation

A fermentation medium of the following formulation was prepared.

| Sucrose | 3.0% |
|---|---|
| Soy flour | 1.5% |
| Corn steep liquor | 0.5% |
| Calcium carbonate | 0.5% |
| Water qs | 100% |

This medium was sterilized and then inoculated with 125 liters of tertiary inoculum, prepared as described in Example 1, per 3000 liters of the above sterile fermentation medium. The fermentation was conducted at 28° C. with a sterile air flow of 6.6 liters per liter of mash, agitation by an impeller operated at 110 rpm and the addition of silicone defoamer agent for 137 hours, at which time the mash was harvested.

EXAMPLE 3

Isolation of LL-D42067β

A total of 4500 liters of harvest mash combined from two fermentations conducted essentially as described in Example 2 was combined with 1% of its volume of diatomaceous earth, mixed for one hour and then the pH was adjusted to 3.0±0.3 with concentrated hydrochloric acid. One half the mash volume of ethyl acetate was added and this mixture was stirred for 3 hours. Diatomaceous earth equal to 5% of the mash volume was added and the mixture was filtered. The ethyl acetate phase of the filtrate was separated, washed with 5% aqueous sodium bicarbonate and then concentrated to a syrup. This material was partitioned between heptane:methanol (2:1).

The 4.5 liters of methanol phase was concentrated to a residue which was triturated with hexane. The hexane was decanted and the residue concentrated to dryness. This material was purified by preparative reverse phase HPLC with the following conditions:

Column: A single PrepPak ®-500/$C_{18}$ Cartridge (a 380 g silica-based octadecyl ($C_{18}$) bonded phase packing material (dimensions: 5.7 cm×30 cm), registered trademark of Waters Associates, Inc., Milford MA)

Mobile Phase
 1: Acetonitrile:water:acetic acid (8,000:12,000:10).
 2: Acetonitrile:water:acetic acid (3,000:6,000:5).
Flow Rate: 50 ml/minute.
Fractionation: 200 ml/fraction.
Sample Load: 2–3 g per 30 ml injection.

Using mobile phase 1, LL-D42067β was found in fractions 7–10. These fractions were combined and evaporated in vacuo to remove the bulk of acetonitrile. The resulting aqueous suspension was treated with an equal volume of ethyl acetate. The ethyl acetate phase was separated and sequentially washed with equal volumes of 5% aqueous sodium bicarbonate, 0.1N hydrochloric acid and twice with water. The organic phase was dried over anhydrous sodium sulfate and evaporated to a solid.

This solid was rechromatographed using mobile phase 2. In this mobile phase LL-D42067β was found in fractions 15–21 which were combined and treated as described above, giving pure LL-D42067β as a yellow solid.

We claim:
1. The compound designated as LL-D42067β wherein the compound has:
 (a) the relative stereochemistry and structure:

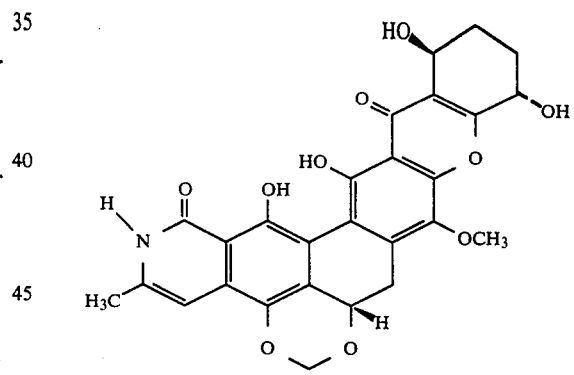

(b) a molecular weight of 521 (FAB-MS);
 (c) a molecular formula: $C_{27}H_{23}NO_{10}$;
 (d) a specific optical rotation: $[\alpha]_D^{26} = +770 \pm 10°$ (C 0.165, DMF);
 (e) characteristic ultraviolet absorption spectra as shown in FIG. I of the attached drawings;
 (f) a characteristic infrared absorption spectrum as shown in FIG. II of the attached drawings;
 (g) a characteristic proton nuclear magnetic resonance spectrum as shown in FIG. III of the attached drawings; and
 (h) a characteristic carbon-13 nuclear magnetic resonance spectrum as shown in FIG. IV of the attached drawings with significant peaks at: 19.1; 25.9; 26.9; 29.7; 62.0; 62.2; 65.0; 72.8; 91.1; 100.1; 110.5; 110.6; 111.7; 114.7; 119.2; 127.2; 128.8; 136.1; 136.3; 137.0; 138.1; 148.9; 151.9; 153.0; 165.3; 167.2; 183.6.

\* \* \* \* \*